US006820019B1

(12) United States Patent
Kelly et al.

(10) Patent No.: US 6,820,019 B1
(45) Date of Patent: Nov. 16, 2004

(54) DEVICE AND METHOD FOR DETERMINING AND COMMUNICATING THE REMAINING LIFE OF A BATTERY IN AN IMPLANTABLE NEUROLOGICAL TISSUE STIMULATING DEVICE

(75) Inventors: Kevin J. Kelly, Shoreview, MN (US); Nathan A. Torgerson, Mounds View, MN (US)

(73) Assignee: Medtronic, Inc., Minneapolis, MN (US)

( * ) Notice: Subject to any disclaimer, the term of this patent is extended or adjusted under 35 U.S.C. 154(b) by 0 days.

(21) Appl. No.: 09/364,967

(22) Filed: Jul. 31, 1999

(51) Int. Cl.$^7$ ................................................. A61N 1/39
(52) U.S. Cl. ............................ 702/63; 320/132; 607/29
(58) Field of Search ........................ 702/57, 58, 60–65, 702/81–82, 108, 117, 124, 126, 127, 179, 181–185, 187, 188, FOR 103–104, FOR 116, FOR 134–135, FOR 137, FOR 140, FOR 170–171; 324/426–428; 320/132, 134, 136; 700/286, 297, 298; 607/29, 32

(56) References Cited

U.S. PATENT DOCUMENTS

| | | | | |
|---|---|---|---|---|
| 4,026,305 A | * | 5/1977 | Brownlee et al. | 128/419 PT |
| 4,041,955 A | * | 8/1977 | Kelly et al. | 128/419 P |
| 4,071,032 A | * | 1/1978 | Schulman | 128/419 P |
| 4,082,097 A | * | 4/1978 | Mann et al. | 128/419 PS |
| 4,142,533 A | * | 3/1979 | Brownlee et al. | 128/419 PT |
| 4,248,237 A | * | 2/1981 | Kenny | 128/419 P |
| 4,254,775 A | * | 3/1981 | Langer | 128/419 D |
| 4,313,079 A | | 1/1982 | Lee | |
| 4,373,527 A | | 2/1983 | Fischell | |
| 4,390,020 A | | 6/1983 | Herpers | |

(List continued on next page.)

FOREIGN PATENT DOCUMENTS

| | | |
|---|---|---|
| WO | WO91/10471 | 7/1991 |
| WO | WO96/20754 | 7/1996 |

(List continued on next page.)

OTHER PUBLICATIONS

Product Brochure: "SynchroMed® Infusion System", Medtronic, Inc. (1995).
Telectronics Model 1254 Physician Manual.
875E Software Guide for Thera; pp. 4–6 and 4–7.

*Primary Examiner*—Marc S. Hoff
*Assistant Examiner*—Carol S. W. Tsai
(74) *Attorney, Agent, or Firm*—IPLM Group, P.A.

(57) ABSTRACT

The invention is a device and method for determining the current status and remaining life of a power source in an implantable neurological tissue stimulator. The invention contemplates a method, performed in a system without human intervention, that includes the steps of assessing the power source voltage of the power source in an IPG, determining, using the power source voltage, where in the power source life cycle the power source is, and taking action in response to the determination of where in the power source life cycle the power source is. The invention also includes a device that embodies the method described above. The device, which is partially resident in an IPG and partially resident in an external device such as a programmer measures the power source voltage in the IPG, using the power source voltage determines where in the power source life cycle the power source is and takes appropriate action in response to the determination of where in the power source life cycle the power source is. A processor, either on the IPG or in the programmer is the preferred structure for determining where in the power source life cycle the power source is and for directing the appropriate action in response to the determination of where in the power source life cycle the power source is.

42 Claims, 8 Drawing Sheets

U.S. PATENT DOCUMENTS

| | | | | |
|---|---|---|---|---|
| 4,448,197 A | | 5/1984 | Nappholz et al. | |
| 4,542,532 A | | 9/1985 | McQuilkin | 455/78 |
| 4,550,370 A | | 10/1985 | Baker | 364/413 |
| 4,556,061 A | * | 12/1985 | Barreras et al. | 607/32 |
| RE32,361 E | * | 2/1987 | Duggan | 128/696 |
| 4,677,363 A | * | 6/1987 | Kopmann | 320/44 |
| 5,080,096 A | | 1/1992 | Hooper et al. | 128/419 R |
| 5,107,833 A | | 4/1992 | Barsness | 128/419 PT |
| 5,117,825 A | | 6/1992 | Grevious | 128/419 PG |
| 5,127,404 A | | 7/1992 | Wyborny et al. | 128/419 P |
| 5,168,871 A | | 12/1992 | Grevious | 128/419 PT |
| 5,292,343 A | | 3/1994 | Blanchette et al. | |
| 5,314,450 A | | 5/1994 | Thompson | |
| 5,324,315 A | | 6/1994 | Grevious | 607/60 |
| 5,344,431 A | * | 9/1994 | Merritt et al. | 607/29 |
| 5,350,411 A | | 9/1994 | Ryan et al. | 607/32 |
| 5,354,319 A | | 10/1994 | Wyborny et al. | |
| 5,369,364 A | | 11/1994 | Renirie et al. | |
| 5,370,668 A | | 12/1994 | Shelton et al. | |
| 5,383,909 A | | 1/1995 | Keimel | 607/7 |
| 5,391,193 A | | 2/1995 | Thompson | |
| 5,402,070 A | | 3/1995 | Shelton et al. | |
| 5,402,794 A | | 4/1995 | Wahlstrand et al. | 128/696 |
| 5,411,537 A | * | 5/1995 | Munshi et al. | 607/33 |
| 5,458,624 A | * | 10/1995 | Renirie et al. | 607/29 |
| 5,591,217 A | * | 1/1997 | Barreras | 607/61 |
| 5,620,474 A | | 4/1997 | Koopman | |
| 5,693,076 A | | 12/1997 | Kaemmerer | 607/59 |
| 5,741,307 A | * | 4/1998 | Kroll | 607/5 |
| 5,741,313 A | * | 4/1998 | Davis et al. | 607/36 |
| 5,744,931 A | * | 4/1998 | Arai et al. | 320/149 |
| 5,752,976 A | | 5/1998 | Duffin et al. | 607/32 |
| 5,766,232 A | | 6/1998 | Grevious et al. | 607/60 |
| 5,769,873 A | * | 6/1998 | Zadeh | 607/29 |
| 5,769,877 A | * | 6/1998 | Barreras | 607/61 |
| 5,807,397 A | * | 9/1998 | Barreras | 607/61 |
| 5,861,019 A | | 1/1999 | Sun et al. | 607/60 |
| 5,904,708 A | | 5/1999 | Goedeke | 607/18 |
| 5,994,876 A | * | 11/1999 | Canny et al. | 320/132 |
| 6,016,448 A | | 1/2000 | Busacker et al. | |
| 6,099,495 A | * | 8/2000 | Kinghorn et al. | 604/93 |
| 6,108,579 A | * | 8/2000 | Snell et al. | 607/29 |
| 6,112,116 A | * | 8/2000 | Fischell et al. | 600/517 |
| 6,148,235 A | * | 11/2000 | Kuiper | 607/29 |
| 6,154,675 A | | 11/2000 | Juran et al. | |
| 6,166,518 A | * | 12/2000 | Echarri et al. | 320/106 |
| 6,167,309 A | * | 12/2000 | Lyden | 607/29 |
| 6,185,461 B1 | | 2/2001 | Er | |
| 6,198,968 B1 | * | 3/2001 | Prutchi et al. | 607/9 |
| 6,272,379 B1 | * | 8/2001 | Fischell et al. | 607/5 |
| 6,400,988 B1 | * | 6/2002 | Gurewitsch | 607/29 |
| 6,490,484 B2 | | 12/2002 | Dooley et al. | |
| 6,584,355 B2 | | 6/2003 | Stessman | |
| 2002/0181328 A1 | | 10/2002 | Rogers | |
| 2003/0065366 A1 | | 4/2003 | Merritt et al. | |

FOREIGN PATENT DOCUMENTS

| | | |
|---|---|---|
| WO | WO 96/20754 | 7/1996 |
| WO | WO01/08749 | 2/2001 |
| WO | WO00/24459 | 5/2002 |
| WO | WO02/49718 | 6/2002 |
| WO | WO 02/074368 A1 | 9/2002 |

* cited by examiner

| Battery Capacity | |
|---|---|
| Remaining Look-up Table | |
| voltage | REMAINING (%) |
| 4.00 | 100 |
| 3.90 | 100 |
| 3.80 | 100 |
| 3.71 | 100 |
| 3.63 | 100 |
| 3.55 | 100 |
| 3.47 | 100 |
| 3.39 | 100 |
| 3.32 | 100 |
| 3.25 | 100 |
| 3.18 | 100 |
| 3.12 | 100 |
| 3.06 | 100 |
| 3.00 | 100 |
| 2.94 | 100 |
| 2.89 | 100 |
| 2.84 | 70 |
| 2.79 | 67.5 |
| 2.74 | 62.5 |
| 2.69 | 57.5 |
| 2.64 | 47.5 |
| 2.60 | 37.5 |
| 2.56 | 35 |
| 2.52 | 32.5 |
| 2.48 | 30 |
| 2.44 | 20 |
| 2.40 | 15 |
| 2.36 | 12.5 |
| 2.33 | 10 |
| 2.29 | 10 |
| 2.26 | 8.5 |
| 2.23 | 6.5 |
| 2.20 | 6 |
| 2.17 | 5.5 |
| 2.14 | 5 |
| 2.11 | 4 |
| 2.08 | 3.5 |
| 2.05 | 3 |
| 2.03 | 2.5 |
| 2.00 | 2 |
| 1.97 | 1.5 |
| 1.95 | 1 |
| <1.90 | 0.5 |

Fig. 5

| Battery Capacity Used Look-up Table | |
|---|---|
| voltage | USED (%) |
| 4.00 | 0 |
| 3.90 | 0 |
| 3.80 | 0 |
| 3.71 | 0 |
| 3.63 | 0 |
| 3.55 | 0 |
| 3.47 | 0 |
| 3.39 | 0 |
| 3.32 | 0 |
| 3.25 | 0 |
| 3.18 | 0 |
| 3.12 | 0 |
| 3.06 | 0 |
| 3.00 | 0 |
| 2.94 | 0 |
| 2.89 | 0 |
| 2.84 | 30 |
| 2.79 | 32.5 |
| 2.74 | 37.5 |
| 2.69 | 42.5 |
| 2.64 | 52.5 |
| 2.60 | 62.5 |
| 2.56 | 65 |
| 2.52 | 67.5 |
| 2.48 | 70 |
| 2.44 | 80 |
| 2.40 | 85 |
| 2.36 | 87.5 |
| 2.33 | 90 |
| 2.29 | 90 |
| 2.26 | 91.5 |
| 2.23 | 93.5 |
| 2.20 | 94 |
| 2.17 | 94.5 |
| 2.14 | 95 |
| 2.11 | 96 |
| 2.08 | 96.5 |
| 2.05 | 97 |
| 2.03 | 97.5 |
| 2.00 | 98 |
| 1.97 | 98.5 |
| 1.95 | 99 |
| <1.90 | 99.5 |

Fig. 6

DEVICE AND METHOD FOR DETERMINING AND COMMUNICATING THE REMAINING LIFE OF A BATTERY IN AN IMPLANTABLE NEUROLOGICAL TISSUE STIMULATING DEVICE

BACKGROUND OF THE INVENTION

1. Field of the Invention

The invention relates to a device and method for determining and communicating the remaining life of a battery or other power source in a device for electrically stimulating neurological tissue.

2. Description of Related Art

Implantable devices exist that electrically stimulate neurological tissue to treat or relieve the symptoms of a wide variety of physiological or psychological maladies or pain. Such devices are typically part of systems that are entirely implantable within the patient or are partially implantable and partially external to the patient. Systems that are entirely implantable in the patient typically include an implantable pulse generator (IPG) and an extension and lead or leads. In such a system, the IPG, extension and lead are entirely implanted in the bodies of the patients. An example of such a system is the Itrel® 3 system manufactured and sold by Medtronic, Inc. of Minneapolis, Minn.

A programmer is used outside the patient's body and communicates with the IPG by both sending and receiving information to and from the IPG. The programmer is used to set and adjust the system, including the parameters of the stimulation pulses, to be most therapeutically effective. This programmer typically includes a computer, programming head and a printer. The programming head is placed over the IPG to program desired system settings using radiowaves. The programming head also receives information from the IPG such as the current electrical pulse parameters or status information. This procedure is done through the skin.

Because the IPG is implanted, the power sources needed to power the IPG is also implanted. Typically, the power source for an IPG is a battery.

Systems that are partially implantable and partially external to the patient include so called "radio frequency" (RF) systems. An example of such an RF system is the Mattrix® system manufactured and sold by Medtronic, Inc. of Minneapolis, Minn. This RF system comprises an external transmitter, an antenna coupled to the external transmitter, an implanted receiver and a lead or leads. The receiver and leads are implanted in the patient's body. The external transmitter generates a series of electrical pulses according to a defined therapeutic pattern. The pulses are passed to the antenna where they are transmitted to the implanted receiver in the patient's body. The implanted receiver passes the pulses to the lead or leads where the pulses are applied to the tissue that is to be stimulated.

One main difference between an entirely implantable system and a RF system is the battery location. The totally implantable system uses a battery that is placed beneath the skin so that no part of the system is outside the body. The radio frequency system uses a battery that is worn outside the body to power the system.

The lead, whether in an RF or IPG system, is a small medical wire with special insulation and contains a set of electrodes (small electrical contacts) through which electrical stimulation is delivered to tissue. The lead is implanted in the patient's body and the electrodes are placed next to the tissue that is desirable to electrically stimulate. The extension is a small cable that is placed under the skin and connects the lead to the IPG.

Many systems, both IPG and RF, allow the patient to partially control their electrical stimulation through a device known as a patient programmer. The patient programmer is a hand-held device that allows the patient to change or control their electrical stimulation within preset bounds. This device allows the patient to adjust the electrical stimulation using radio waves between visits to the doctor.

FIG. 1 schematically shows an implantable system such as the Itrel® 3 system including a programmer. As can be seen, the system, generally labeled 2 has an IPG 4, an attached extension 6, a lead 8 attached to extension 6 and an external programmer 10. The IPG 4 has a battery 12 that powers the device and provides the power for the electrical stimulation pulses that are provided to the lead 8 through extension 6 to be applied to the tissue that is to be electrically stimulated. IPG 4 also has a battery voltage determining system 13 that determines the voltage of battery 12.

IPG 4 also includes an IPG telemetry system 14 that receives information from the programmer telemetry system 16 of the programmer 10. Through programmer telemetry system 16, programmer 10 sends commands to the IPG 4 through the IPG telemetry system 14 to change the parameters of the stimulation pulses produced by the IPG 4. In return, IPG 4, through IPG telemetry system 14, sends information to programmer 10, through the programmer telemetry system 16, regarding the current status of the IPG 4 including current parameter settings and the voltage of the battery 12.

In the Itrel® 3 system, the battery is a Lithium Thionyl Chloride battery. FIG. 2 shows the voltage versus capacity chart for this type of battery. As can be seen, the battery voltage remains virtually constant through most of the life of the battery. At approximately the last 5% of battery life, the battery voltage drops rapidly. Therefore, by tracking the battery voltage, it can be determined that the battery is in its last 5% of life when the voltage drops rapidly. Unfortunately, because the battery voltage is virtually flat for the first 95% of battery life, it is difficult if not impossible to determine where in the battery life cycle the battery is during the first 95% of battery life.

As stated above, IPG 4, through IPG telemetry system 14, sends information to programmer 10, through the programmer telemetry system 16, regarding the voltage of the battery 12. The physician takes this battery voltage information and consults a "look-up" table showing battery voltages and corresponding remaining battery capacity values. While the battery voltage is "high" and constant, as during the first 95% of battery life, the physician is only able to determine that the battery is somewhere in its first 95% of life. Only when the battery voltage begins to drop can the physician ascertain that the battery is in the last 5% of its life.

Many batteries have battery capacity versus voltage profiles similar to that shown in FIG. 3. As can be seen, these profiles are not "flat" along a substantial portion of the battery life. Instead, there are distinct values correlating the measured battery voltage and the battery capacity used or remaining. It is highly desirable to have a system that allows the user to ascertain either the battery capacity already used or battery capacity remaining in batteries having battery capacity versus voltage profiles similar to that shown in FIG. 3.

SUMMARY OF THE INVENTION

The invention is a device and method for determining and communicating the remaining life of a battery or other power source in an implantable neurological tissue stimulator. Basically, the invention contemplates a method, performed in a system without human intervention, that includes the steps of assessing the voltage of a battery or other power source in an IPG, determining, using the voltage, where in the battery or other power source life cycle the battery or other power source is, and taking action in response to the determination of where in the life cycle the battery or other power source is.

The invention also includes a device that embodies the method described above. The device, which may be either totally resident in an IPG or partially resident in an IPG and partially resident in an external device such as a programmer, measures the power source voltage in the IPG, uses the power source voltage to determine where in the power source life cycle the power source is and takes appropriate action in response to the determination of where in the power source life cycle the power source is. A processor, either on the IPG or in the programmer or patient programmer is the preferred structure for determining where in the power source life cycle the power source is and for directing the appropriate action in response to the determination of where in the power source life cycle the power source is.

It is therefore a primary object of the invention to provide a device that determines the current status and remaining life of a power source in an implantable neurological tissue stimulator.

It is therefore a primary object of the invention to provide a device that determines the current status and remaining life of a power source in an implantable neurological tissue stimulator without immediate human intervention.

It is therefore a primary object of the invention to provide a device that after determining the current status and remaining life of a power source in an implantable neurological tissue stimulator, automatically alerts the physician to the current status and remaining life of the power source.

These and other objects of the invention will be clear from the description of the invention given herein and particularly with reference to the attached drawings and the Detailed Description of the Invention. Throughout this description, like reference numbers refer to like elements.

BRIEF DESCRIPTION OF THE DRAWINGS

FIG. 5 is a "look-up" table as used in the preferred embodiment of the present invention.

FIG. 6 is a "look-up" table as used in an alternate embodiment of the present invention.

DETAILED DESCRIPTION OF THE INVENTION

Figure 1:
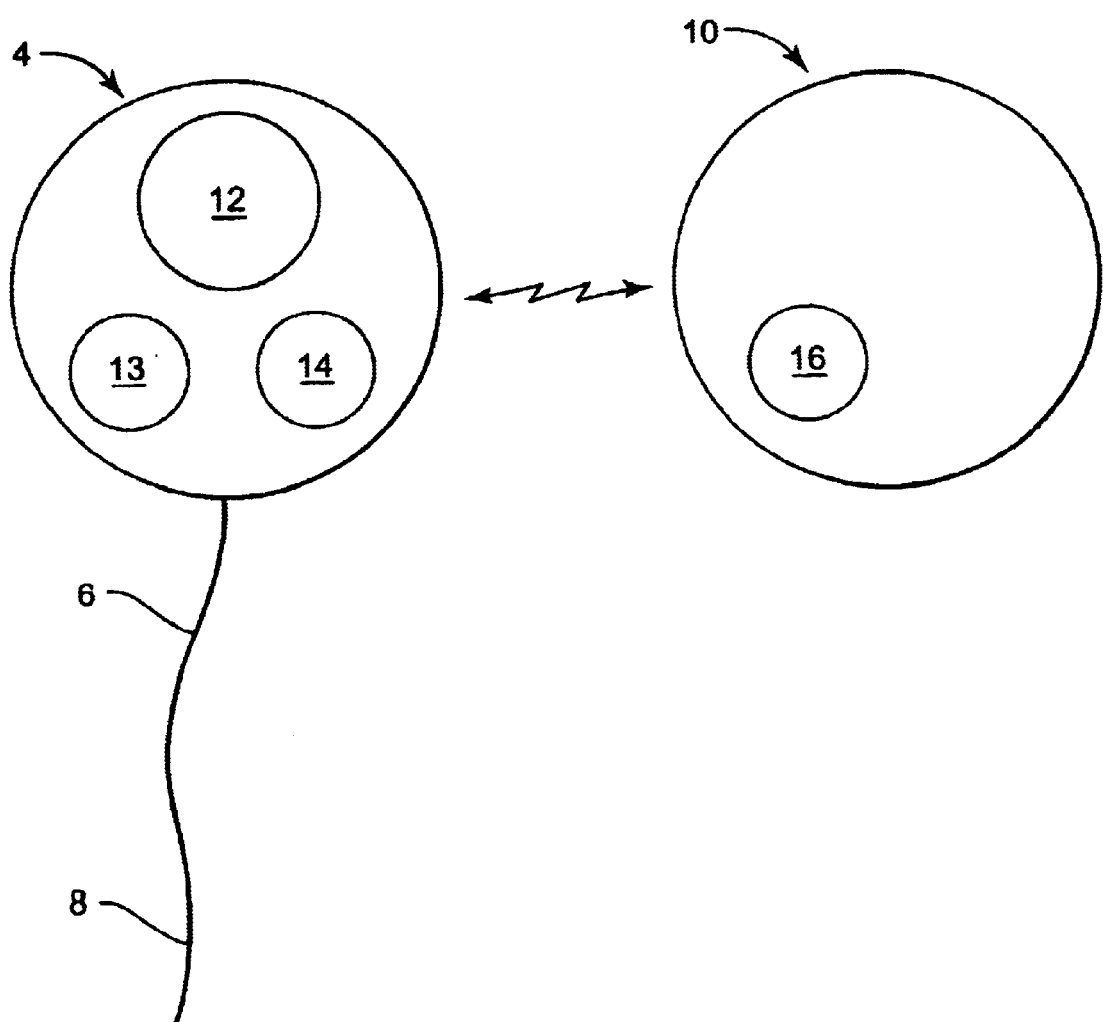
FIG. 1 is a schematic drawing of an IPG system.
Figure 2:
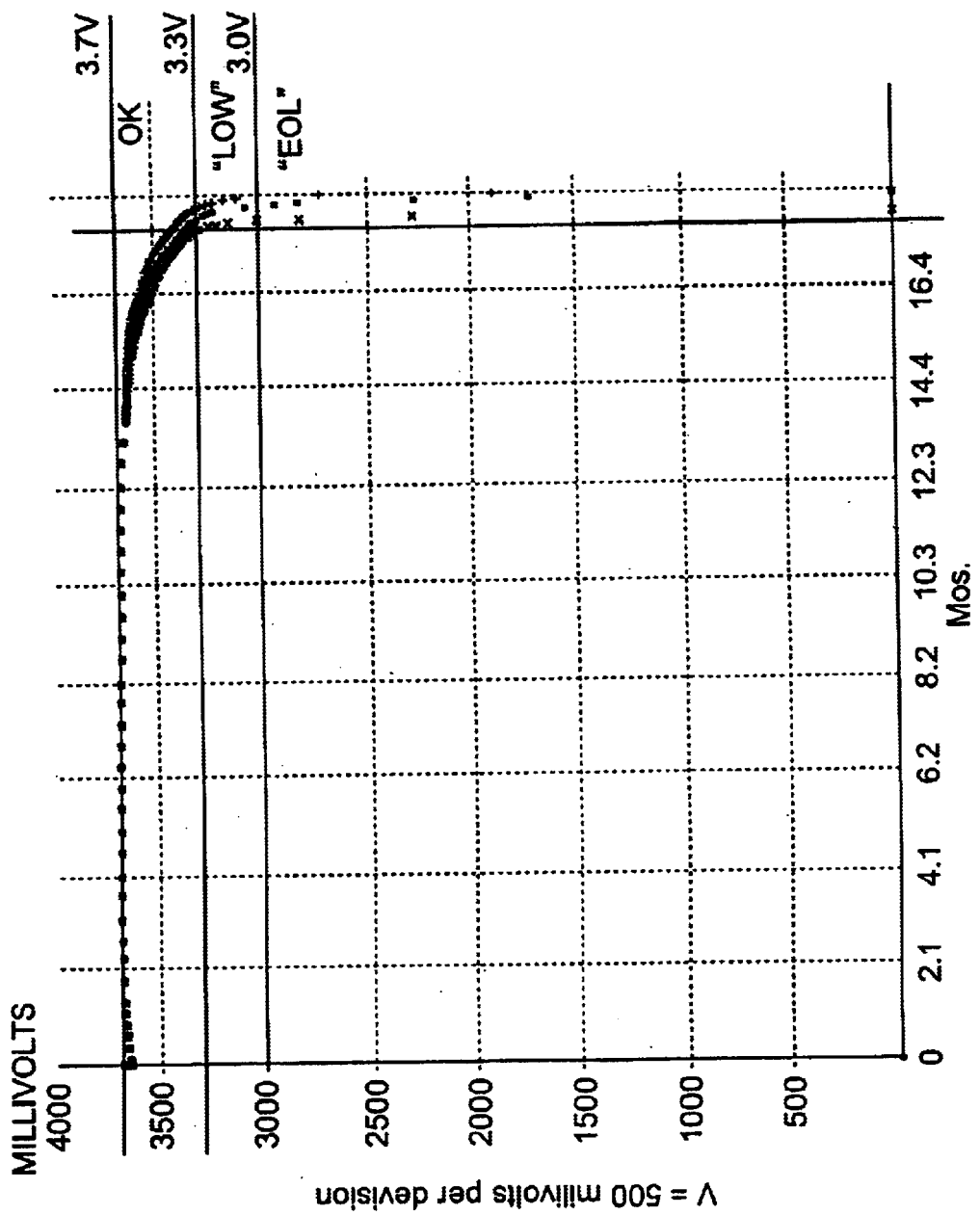
FIG. 2 is a chart showing the voltage versus capacity of a Lithium Thionyl Chloride battery.
Figure 3:
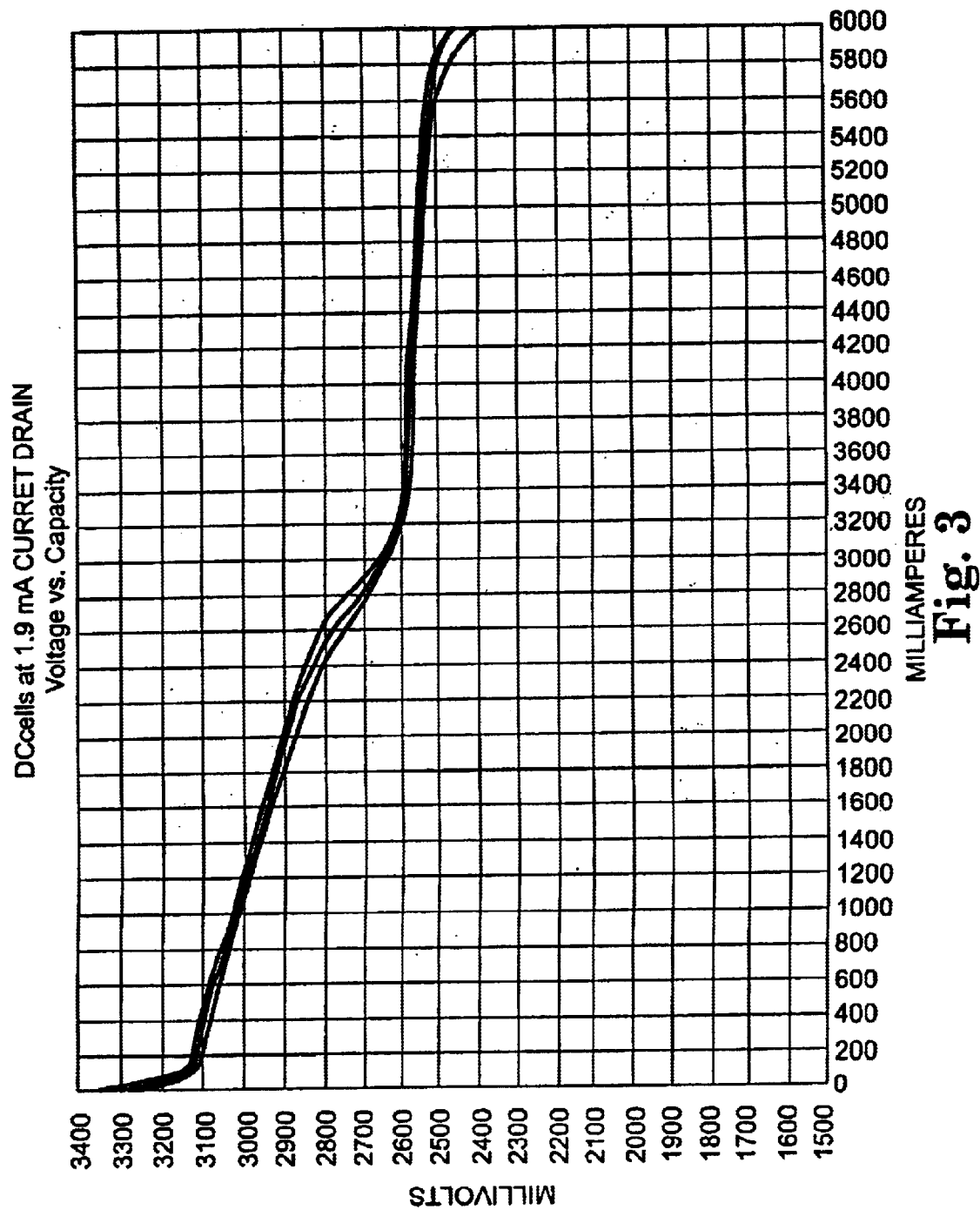
FIG. 3 is a chart showing the voltage versus capacity of a Lithium Combination Silver Vanadium Oxide (CSVO) battery.
Figure 4:
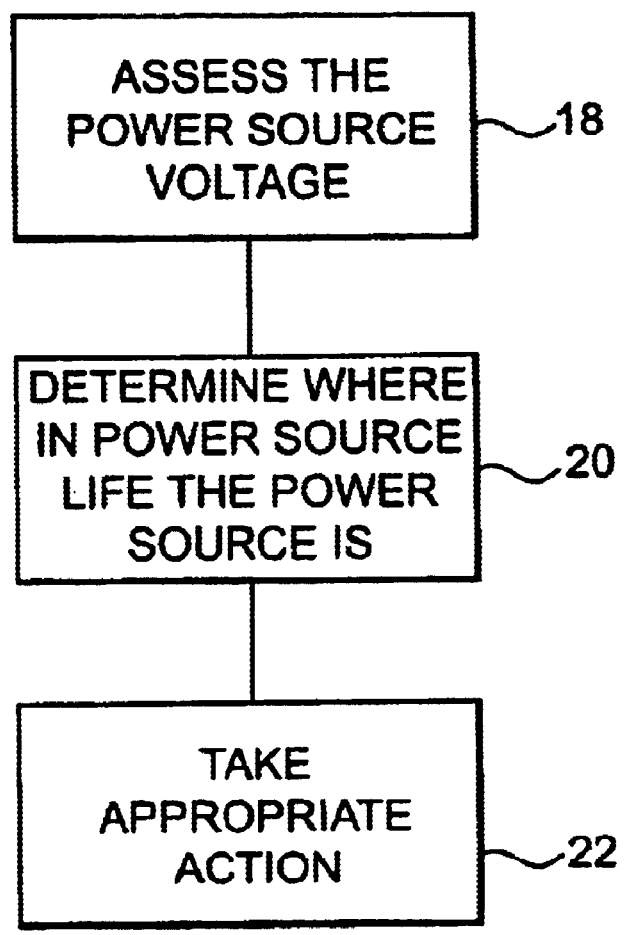
FIG. 4 is a flow chart of the operation of the present invention.

FIG. 4 is a flow chart of the method of the present invention. Examples of devices to implement the method are described in detail below. The method, in its broadest form, begins at step 18 with assessing the voltage of the power source in an implantable neurological tissue stimulator. The program passes to step 20 where this voltage is used to determine where the power source is in the power source life cycle. The program then passes to step 22 where the system takes appropriate action in response to the determination of where the power source is in the power source life cycle.

Throughout the description of the invention herein, reference to a "power source", unless specifically stated otherwise, refers to batteries, capacitors or any other source of electrical power as will be clear to those skilled in the art. In the preferred embodiment, the power source for the implantable neurological tissue stimulator is a battery but other power sources could also be used.

Assessing the voltage of the power source in step 18 can be done according to any of the well known methods for assessing voltages as will occur to those skilled in the art. Examples of such methods include the well known use of an analog to digital (A/D) converter.

In step 20, there are several ways to determine where in the power source life cycle a power source is. The preferred method is uses a "look-up table" that correlates the voltage assessed in step 18 to a predetermined "power source capacity remaining" value. The "power source capacity remaining" values and their correlation to corresponding power source voltages are determined ahead of time by experimentation. It may be easier to determine the power source capacity remaining by measuring the power source capacity used and then subtracting this value from the total power source capacity determined experimentally for this power source type.

An example of such a "look-up table" is given in FIG. 5. The "look-up table" is in the form of a matrix where power source voltage values, in this case battery voltage values, are listed in a first column and corresponding "battery capacity remaining" values are listed in a parallel column where the "battery capacity remaining" value is next to its corresponding battery voltage value.

An alternate way to determine where in the power source life cycle a power source is also uses a "look-up table". However, in this embodiment, the "look-up" table correlates the power source voltage assessed in step 18 to a predetermined and pre-measured "power source capacity used" value. The "power source capacity used" values and their correlation to corresponding power source voltages are determined ahead of time by experimentation. It may be easier to determine the power source capacity used by calculating the power source capacity remaining and then subtracting this value from the total power source capacity determined experimentally for this power source type.

An example of such a "look-up table" for this alternate embodiment is given in FIG. 6. The "look-up table" is in the form of a matrix where power source voltage values, in this case battery voltage values, are listed in a first column and corresponding "battery capacity used" values are listed in a parallel column where the "battery capacity used" value is next to its corresponding battery voltage value.

Another alternate way to determine where in the battery life cycle a power source is uses a formula to determine either the power source capacity remaining or the power source capacity used. The formula for this method is found experimentally by correlating measured power source voltages and corresponding power source capacity remaining values or power source capacity used values. For example, the formula for the relationship between the measured battery voltages and the corresponding battery capacity remaining values shown in the chart of FIG. 5 is:

Remaining Battery Capacity=−115+62.4 Battery Voltage where the battery voltage varies between 0 volts and 4 volts for this type of battery. The formula for the relationship between the measured battery voltages and the corresponding battery capacity used values shown in the chart of FIG. 6 is:

Battery Capacity Used=229−65.8 C3 Battery Voltage where the battery voltage also varies between 0 volts and 4 volts for this type of battery.

A possible problem with this approach is that the formula is a linear formula whereas many relationships between power source voltage and remaining power source capacity are not linear. As a result, where the relationship between power source voltage and the remaining power source capacity is not linear, a linear approximation of remaining power source capacity will be only an approximation.

Alternately, a formula may be developed for determining the relationships between power source voltage and remaining power source capacity that is non-linear. Such non-linear formulas can be developed, for example, by using least squares approximations with high order polynomials or by using cubic splines techniques as will be well understood by those skilled in the art. Where the relationship between power source voltage and the remaining power source capacity is not linear, such non-linear formulas, appropriately chosen, may closely approximate the actual relationship between measured power source voltage and remaining power source capacity.

Appropriate action in block 22 can include such things as simply informing the user of where in the power source life the power source is. This can be done by displaying a representation of the percentage of power source capacity used or remaining. Alternately or in addition, if the remaining power source capacity falls within a predetermined limit, an alarm can be triggered to alert the user of this status. The alarm can take the form of an audible or visible warning such as a warning chime or a flashing visual display panel, a physical warning such as a vibrating alarm or other means of alerting the user or emphasizing the status as will occur to those skilled in the art. Appropriate action can also include taking no action obvious to the user. This action may be desirable if the remaining power source capacity is well outside of predetermined limits.

The steps of the method described above can either be done entirely in an implantable neurological tissue stimulator or done partially in an implantable neurological tissue stimulator and an external device such as a programmer. In the latter case, because the power source for the implantable neurological tissue stimulator is part of the implantable neurological tissue stimulator, the step of assessing the voltage of the power source in an implantable neurological tissue stimulator will probably be, although is not required to be, done at the power source on the implantable neurological tissue stimulator. However, the remaining step may either be performed on the implantable neurological tissue stimulator or on an external device such as a programmer or patient programmer.

Figure 7:
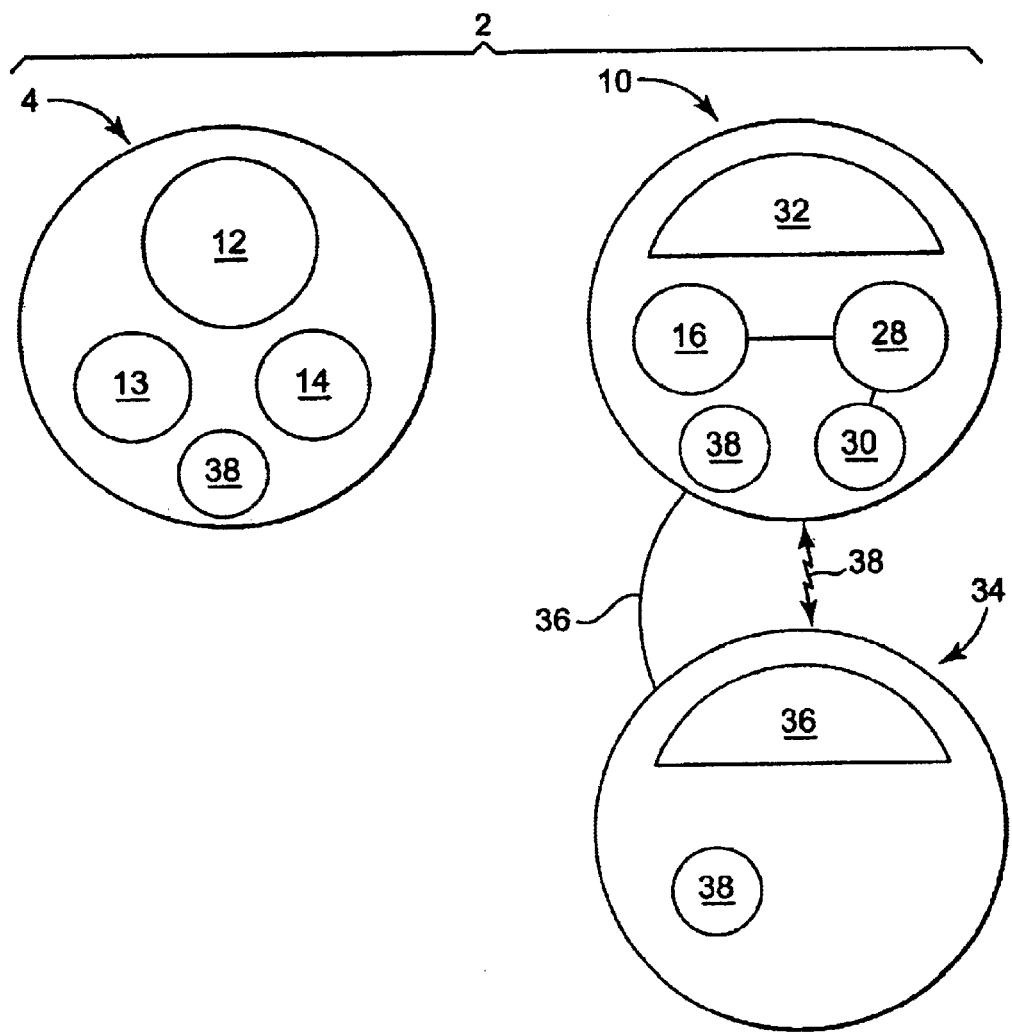
FIG. 7 is a schematic view of the preferred embodiment of the present invention.

Referring to FIG. 7, the preferred embodiment of the device of the invention to implement the method described above is shown. As described above, IPG 4 includes a voltage determining system 13 and an IPG telemetry system 14. Voltage determining system 13 measures the voltage of the battery 12 that powers IPG 4 by means well known in the art including, but not limited to using an analog to digital (A/D) converter. Once the voltage of battery 12 has been determined by voltage determining system 13, the battery voltage information is passed to the IPG telemetry system 16.

IPG telemetry system 16 sends the battery voltage information from the IPG 4 to programmer 10 by telemetry means well understood in the art. Examples of telemetry systems include, but are not limited to, those described in U.S. Pat. No. 4,231,027 issued to Brian M. Mann and Russell R. Beane on Oct. 28, 1980 and entitled "BATTERY MONITORING MEANS FOR AN IMPLANTABLE LIVING TISSUE STIMULATOR" and U.S. Pat. No. 5,752,977 issued to John J. Grevious, Robert A. Neumann and Koen J. Weijand on May. 19, 1998 entitled "EFFICIENT HIGH DATA RATE TELEMETRY FORMAT FOR IMPLANTED MEDICAL DEVICE", the teachings of which are incorporated herein by reference in their entirety.

Programmer 10 receives the battery voltage information from IPG 4 through programmer telemetry system 16. Programmer telemetry system 16 passes the battery voltage information to a processor 28. Processor 28 includes a memory 30 that includes a "look-up" table embedded with correlated information about the battery voltage and the corresponding battery capacity information. Memory 30 may be either volatile such as RAM or read-only such as EEPROM or other types as will occur to those skilled in the art.

This battery capacity information may be either the battery capacity used or the battery capacity remaining. An example of such a "look-up" table is shown in FIG. 5 for a Lithium Combination Silver Vanadium Oxide (CSVO) battery. In this example, the battery capacity information is battery capacity used. In either case, either the battery capacity used or battery capacity remaining is determined experimentally by correlating measured battery voltages with either the measured battery capacity used or the measured battery capacity remaining. Thereafter, the battery voltages and the corresponding battery capacity information, whether battery capacity used or battery capacity remaining, are loaded into memory 30 through the "look-up" table.

The "look-up" table may contain both battery capacity used information and battery capacity remaining information. In such a case, the "look-up" table would have three columns instead of two; the additional column containing the additional battery capacity information. Alternately, if either the battery capacity used information or the battery capacity remaining information is stored in the "look-up" table, the other battery capacity information can be calculated. For example, if remaining battery capacity is stored in the "look-up" table, the used battery capacity can be determined by simply subtracting the remaining battery capacity from the estimated total battery capacity. Conversely, if used battery capacity is stored in the "look-up" table, the remaining battery capacity can be determined by simply subtracting the used battery capacity from the estimated total battery capacity.

Processor 28 correlates the battery voltage information received from IPG 4 to the battery capacity values in the "look-up" table stored in memory 30. This battery capacity information, whether used battery capacity or remaining battery capacity, may be displayed to the physician through a display screen 32 on the programmer 18 or may be passed from the programmer to an external computer 34 by direct connection 36 or through telemetry 46 as is well understood in the art. Computer 34 can display the battery capacity information on its display screen 56, record the information or further process the information.

Alternately, or in addition, once the remaining battery capacity information has been determined, this remaining battery capacity information can be used to estimate the remaining life of the battery 12. This is preferably done by first determining the probably usage rate of the battery 12. A simple way to determine this usage rate is to divide the used capacity of the battery by the length of time that the IPG 4 has been working. In this way, an estimate of the battery capacity used per time unit can be obtained. Then, the remaining battery capacity can be divided by this capacity used per time unit amount to arrive at an estimated time remaining before the battery capacity is expended. This calculation is preferably performed by the processor 28 and then the resulting estimate of remaining battery life is displayed on the display screen 30 or passed to computer 34 to be displayed, recorded or further processed.

Although the previously described method for estimating the remaining life time of a battery 12 is simple to implement, the resulting estimate of remaining battery life will be inaccurate if the rate of battery usage is not constant. For example, if the amplitude or frequency of the stimulation pulses provided by the IPG 4 are changed by reprogramming the device prior to calculating the remaining battery life as described above, an estimated remaining battery life will be inaccurate. Therefore, in one embodiment of the invention, the processor 28 in the programmer 10 stores the date of a change in the programming of the IPG 4 and determines and stores the used battery capacity at that time. Then, when determining the probably usage of the battery 12, the used capacity of the battery 12 since the last programming is first determined. This is done by determining the current used battery capacity and subtracting it from the previously stored used battery capacity at the time of the programming change. In this way, the battery capacity used since the programming change is determined.

Once this battery capacity used since the programming change has been determined, this battery capacity used is divided by the length of time since the IPG 4 has been reprogrammed. In this way, an estimate of the capacity used per time unit can be obtained for the time period since the IPG 4 was reprogrammed. Then, the remaining battery capacity is determined as described above.

The remaining battery capacity can be divided by this capacity used per time unit amount since the IPG 4 was reprogrammed to arrive at an estimated time remaining before the battery capacity is expended. This calculation is preferably performed by the processor 28 and then the resulting estimate of remaining battery life is displayed on the display screen 32 or 36.

An alarm 38, alerts to user to conditions of the power source that are outside of preset parameters. Alarm 38 can take the form of any number of well known alarms providing visual, audible or physical indication that the alarm conditions have been triggered. As described above, alarm 38 can take the form of an audible or visible warning such as a warning chime or a flashing visual display panel, a physical warning such as a vibrating alarm or other means of alerting the user or emphasizing the status as will occur to those skilled in the art. Alarm 38 can be directly connected to processor 28 or may be triggered remotely through telemetry.

Processor 28 and memory 30 has been described heretofore as being located in the programmer 10. Although this is the preferred location, processor 28 and memory 30 may be located on IPG 4 or in computer 32. Further, processor 28 may be located in any of these locations and memory 30 in any other of the locations so long as communication is possible between processor 28 and memory 30.

Figure 8:
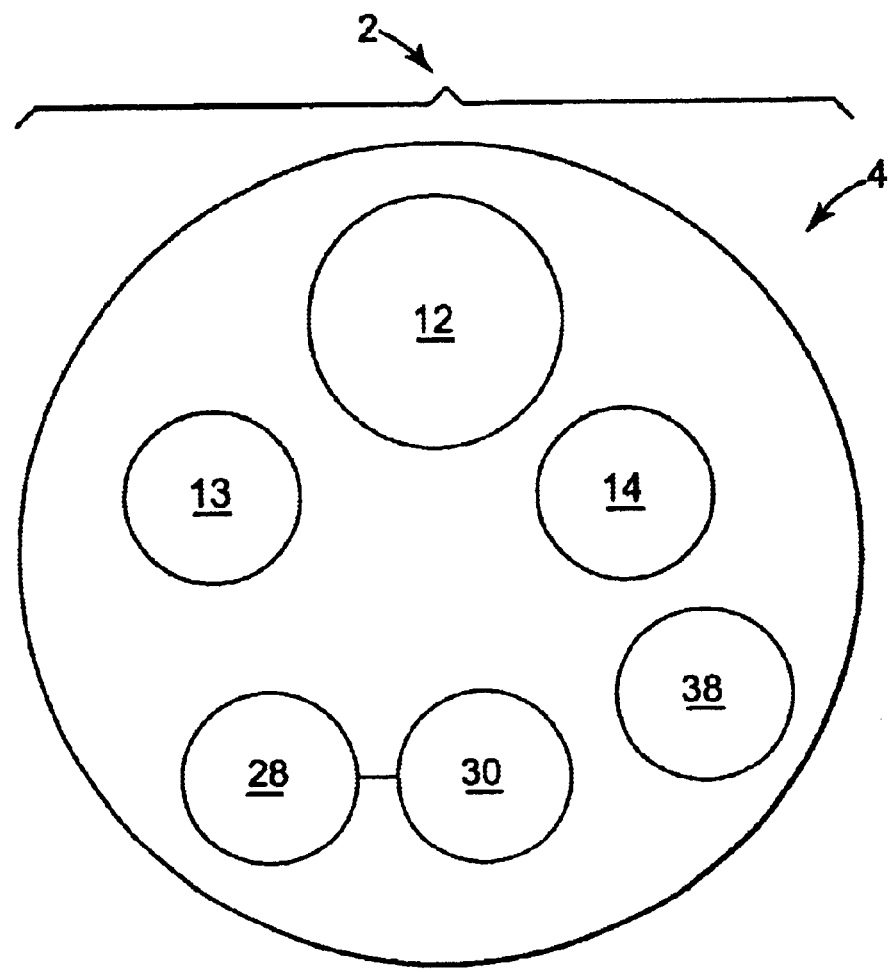
FIG. 8 is a schematic view of an alternate embodiment of the present invention.

An alternate embodiment of the invention, applying these principles, is shown in FIG. 8. This embodiment is identical to the preferred embodiment described above with the exception that the processor 28 and memory 30 are included as part of the IPG 4. In this embodiment, alarm 38 may either be part of the IPG 4 or may be external to IPG 4 and triggered remotely.

The implantable medical device described in detail herein has been an implantable electrical stimulator for electrically stimulating neurological tissue. However, the method and device described herein can also be used in other implantable medical devices so long as the implantable medical devices have an internal power source such as a battery. Examples of such systems include pacemakers, defibrillators and implantable drug pumps to name but a few examples.

Alternately, the invention will also have applicability to implantable medical devices powered by capacitors or so called "super-capacitors". Examples of such systems are disclosed in U.S. Pat. No. 5,807,397 issued to Francisco J. Barreras on Sep. 15, 1998 entitled "IMPLANTABLE STIMULATOR WITH REPLENISHABLE, HIGH VALUE CAPACITIVE POWER SOURCE AND METHOD THEREFOR", U.S. Pat. No. 5,769,877 issued to Francisco J. Barreras on Jun. 23, 1998 entitled "HIGH VALUE CAPACITIVE, REPLENISHABLE POWER SOURCE" and U.S. Pat. No. 5,591,217 issued to Francisco J. Barreras on Jan. 7, 1997 entitled IMPLANTABLE STIMULATOR WITH REPLENISHABLE, HIGH VALUE CAPACITIVE POWER SOURCE AND METHOD THEREFOR", the teachings of which are incorporated herein by reference in their entireties.

The description contained herein is intended to be illustrative and not exhaustive. Many variations and alternatives will occur to one of ordinary skill in this art. All these alternatives and variations are intended to be included within the scope of the attached claims. Those familiar with the art may recognize other equivalents to the specific embodiments described herein which equivalents are also intended to be encompassed by the claims attached hereto.

What is claimed is:

1. A method of determining a remaining life of a power source having a voltage in an implantable medical device comprising the steps of:
   assessing the voltage of the power source though an actual measurement;
   determining, based on the voltage of the power source, capacity information of the power source;
   obtaining a time that the power source has been operating through an actual measurement; and
   determining the remaining life of the power source based on the capacity information of the power source and the time that the power source has been operating.

2. The method of claim 1 wherein the step of assessing the power source voltage utilizes an analog to digital (A/D) converter.

3. The method of claim 1 wherein the step of determining capacity information of the power source comprises determining a remaining power source capacity.

4. The method of claim 1 wherein the step of determining the remaining life of the power source includes the steps of:
   determining a probable usage rate of the power source from the capacity information; and
   dividing a determined remaining capacity by the probable usage rate of the power source.

5. The method of claim 1 wherein the step of determining the remaining life of the power source includes the step of determining the probable usage rate of the power source.

6. The method of claim 5 wherein the step of determining the probable usage rate of the power source includes the step of determining the used capacity of the power source.

7. The method of claim 6 wherein the step of determining the probable usage rate of the power source includes the step of dividing the determined used capacity of the power source by the length of time that the implantable medical device has been working.

8. The method of claim 5 wherein the step of determining the probable usage rate of the power source includes the step of determining the used capacity of the power source since the last time the implantable medical device was reprogrammed.

9. The method of claim 8 wherein the step of determining the probable usage rate of the power source includes the step of dividing the determined used capacity of the power source since the last time the implantable neurological tissue stimulator was reprogrammed by the length of time since the implantable medical device was reprogrammed.

10. The method of claim 1 wherein the step of determining capacity information of the power source includes the step of correlating, in a "look-up table", the power source voltage assessed in the step of assessing the power source voltage to a predetermined "power source capacity remaining" value.

11. The method of claim 1 wherein the step of determining capacity information the power source includes the step of correlating, in a "look-up table", the power source voltage assessed in the the step of assessing the power source voltage to a predetermined "power source capacity used" value.

12. The method of claim 1 wherein the step of determining capacity information of the power source includes the step of determining the power source capacity used and then subtracting this value from the total power source capacitor;
whereby, the power source capacity remaining is determined.

13. The method of claim 1 wherein the step of determining capacity information of the power source includes the step of determining the power source capacity remaining and then subtracting this value from the total power source capacity;
whereby, the power source capacity used is determined.

14. The method of claim 1 wherein the step of determining capacity information of the power source includes the step of calculating use the voltage of the power source determined in the step of assessing the voltage of the power source, the remaining power source capacity by a formula.

15. A method of determining the current status and remaining life of a power source in an implantable medical device comprising the steps of:
assessing the power source voltage of the power source in an implantable medical device;
determining, based on the assessed power source voltage, where the power source is in its power source life cycle by calculating the remaining power source capacity by using a formula of the form: Remaining Battery Capacity=a constant+a constant multiplied by the power source voltage determined in the step of assessing the power source voltage of the power source in an implantable medical device; and
taking appropriate action in response to the determination of where the power source is in its power source life cycle.

16. The method of claim 14 wherein the step of calculating the remaining power source capacity by a formula includes the step of calculating the remaining power source capacity by using a non-linear formula.

17. A method of determining the current status and remaining life of a power source in an implantable medical device comprising the steps of:
assessing the power source voltage of the power source in an implantable medical device;
determining, based on the assessed power source voltage, where the power source is in its power source life cycle by calculating the power source capacity by using a formula of the form: power source capacity used=a constant+a constant multiplied by the power source voltage determined in the step of assessing the power source voltage of the power source in an implantable medical device; and
taking appropriate action in response to the determination of where the power source is in its power source life cycle.

18. The method of claim 1 further comprising the step of informing the user of the status of the power source.

19. The method of claim 18 wherein the step of informing the user includes the step of displaying a representation of the percentage of power source capacity used.

20. The method of claim 18 wherein the step of informing the user includes the step of displaying a representation of the percentage of power source capacity remaining.

21. The method of claim 18 wherein the step of informing the user includes the step of determining whether the remaining power source capacity falls within a predetermined limit.

22. The method of claim 21 wherein the step of determining whether the remaining power source capacity falls within a predetermined limit further includes the step of alerting the user if the remaining power source capacity falls within a predetermined limit.

23. The method of claim 22 wherein the step of alerting the user if the remaining power source capacity falls within a predetermined limit further includes the step of alerting the user by triggering an alarm.

24. The method of claim 23 wherein the step alerting the user by triggering an alarm includes the step of triggering an alarm chosen from the group consisting of audible or visual warnings.

25. A device for determining the status and remaining life of a power source in an implantable neurological tissue stimulator, device comprising:
an implantable neurological tissue stimulator, the implantable neurological tissue stimulator having:
a source of power having a voltage;
a voltage determining system for determining the voltage of the source of power through actual measurement;
a programmer for creating and processing information to be sent to and received from the implantable neurological tissue stimulator, the programmer including a processor and a memory attached thereto;
a system for communicating information between the implantable neurological tissue stimulator and the programmer;
wherein the voltage determining system passes the voltage of the source of power to the system for communication; and
wherein the system for communication passes the voltage of the source of power from the implantable neurological tissue stimulator to the programmer and to the processor, and wherein the processor determines, based on the voltage of the source of power, capacity information of the power source and determines the remaining life of the power source based on the capacity information of the power source and a time that the power source has been operating obtained through an actual measurement.

26. The device of claim 25 wherein the processor determines the capacity information of the power source by correlating the voltage with a remaining capacity value stored in a "look-up" table.

27. The device of claim 25 wherein the processor determines the capacity information of the power source by correlating the voltage with a used capacity value stored in a "look-up" table.

28. The device of claim 25 wherein the processor determines the capacity information of the power source by calculating the remaining capacity of the source of power by using a predetermined formula.

29. The device of claim 25 wherein the processor determines the capacity information of the power source by calculating the used capacity of the source of power by using a predetermined formula.

30. The device of claim 25 wherein the power source is a battery.

31. The device of claim 25 wherein the power source is a capacitor.

32. A method of electrically stimulating nervous tissue in a patient, comprising the steps of:

implanting in the patient a pulse generator having a power source, and a lead connected to the pulse generator;

stimulating nervous tissue with electrical pulses generated by the pulse generator and communicated by the lead;

controlling the pulse generator within preset limits by the patient to adjust stimulation of nervous tissue;

determining the status and remaining life of the power source as set forth in claim 1.

33. A method of electrically stimulating nervous tissue in a patient, comprising the steps of:

implanting in the patient a pulse generator having a power source, and a lead connected to the pulse generator;

stimulating nervous tissue with electrical pulses generated by the pulse generator and communicated by the lead;

controlling the pulse generator within preset limits by the patient to adjust stimulation of nervous tissue;

detecting the status and remaining life of the power source as set forth in claim 19.

34. A method of electrically stimulating nervous tissue in a patient, comprising the steps of:

implanting in the patient a pulse generator having a power source, and at lead connected to the pulse generator;

stimulating nervous tissue with electrical pulses generated by the pulse generator and communicated by the lead;

controlling the pulse generator within preset limits by the patient to adjust stimulation of nervous tissue;

determining the status and remaining life of the power source as set forth in claim 23.

35. The method of claim 1 wherein the step of determining the remaining life of the power source includes the steps of:

determining a probable usage rate of the power source from the capacity information and the time that the power source has been operating; and determining the remaining life of the power source as a function of the capacity information and the probable usage rate.

36. The method of claim 35 wherein said determining the remaining life of the power source step comprises:

determining a remaining capacity of the power source from the capacity information; and calculating the remaining life of the power source by dividing the remaining capacity of the power source by the probable usage rate of the power source.

37. The method of claim 36 wherein said capacity information is a used capacity of the power source.

38. The method of claim 37 wherein the remaining capacity of the power source is determined from the used capacity of the power source.

39. The method of claim 38 wherein the remaining capacity of the power source is determined by subtracting the used capacity of the power source from a total capacity of the power source.

40. The method of claim 36 wherein the probable usage rate is a capacity of the power source used per unit time.

41. The method of claim 36 wherein the determining the remaining capacity of the power source is calculated by using a formula of the form: Remaining Battery Capacity=a constant+a constant multiplied by the voltage of the power source determined in the step of assessing the voltage of the power source.

42. The method of claim 36 wherein the determining the remaining capacity of the power source is calculated by using a formula of the form: power source capacity used=a constant+a constant multiplied by the power source voltage determined in the step of assessing the voltage of the power source.

* * * * *

UNITED STATES PATENT AND TRADEMARK OFFICE
CERTIFICATE OF CORRECTION

PATENT NO. : 6,820,019 B1
DATED : November 16, 2004
INVENTOR(S) : Kevin J. Kelly et al.

It is certified that error appears in the above-identified patent and that said Letters Patent is hereby corrected as shown below:

<u>Column 9,</u>
Line 38, reads "...capacitor;" but should read -- ...capacity; --
Line 49, reads "...calculating use" but should read -- ...calculating, using --

Signed and Sealed this

Third Day of May, 2005

JON W. DUDAS
*Director of the United States Patent and Trademark Office*